US00PP15360P2

(12) United States Plant Patent
Oliver

(10) Patent No.: US PP15,360 P2
(45) Date of Patent: Nov. 23, 2004

(54) ***TIARELLA* PLANT NAMED 'RUNNING TIGER'**

(50) Latin Name: *Tiarella cordifolia*
Varietal Denomination: Running Tiger

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/775,938

(22) Filed: Feb. 10, 2004

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Tiarella* plant named 'Running Tiger', characterized by its full, densely foliated and mounded plant habit; vigorous growth habit; palmately lobed green-colored leaves with dark purple markings; numerous showy white-colored flowers arranged on dense racemes; and excellent garden performance.

2 Drawing Sheets

Botanical classification/cultivar designation: *Tiarella cordifolia* cultivar Running Tiger.

BACKGROUND OF THE INVENTION

The present invention relates to a new and distinct cultivar of *Tiarella* plant, botanically known as *Tiarella cordifolia* and hereinafter referred to by the name 'Running Tiger'.

The new *Tiarella* is a product of a planned breeding program conducted by the Inventor in Scottdale, Pa. The objective of the breeding program is to create new vigorous *Tiarella* cultivars having interesting leaf shape and attractive leaf and flower coloration.

The new *Tiarella* was discovered by the Inventor in a controlled environment in Scottdale, Pa., from seedling progeny from a cross-pollination made by the Inventor in May, 1999, of the *Tiarella cordifolia* cultivar Butterfly Wings, disclosed in U.S. Plant Pat. No. 13,629, as the female, or seed, parent with the *Tiarella cordifolia* cultivar Lace Carpet, not patented, as the male, or pollen, parent. The new *Tiarella* was selected by the Inventor in May, 2000. The selection of this plant was based on its desirable leaf shape and coloration.

Asexual reproduction of the new *Tiarella* by cuttings in a controlled environment in Scottdale, Pa., since May, 2000, has shown that the unique features of this new *Tiarella* are stable and reproduced true to type in successive generations.

SUMMARY OF THE INVENTION

The cultivar Running Tiger has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Running Tiger'. These characteristics in combination distinguish 'Running Tiger' as a new and distinct cultivar.

1. Full and densely foliated; mounded plant habit.
2. Vigorous growth habit.

3. Palmately lobed green-colored leaves with dark purple markings.
4. Numerous showy white-colored flowers arranged on dense racemes.
5. Excellent garden performance.

Plants of the new *Tiarella* can be compared to plants of the female parent, the cultivar Butterfly Wings. In side-by-side comparisons conducted by the Inventor in Scottdale, Pa., plants of the new *Tiarella* differed from plants of the cultivar Butterfly Wings in the following characteristics:

1. Plants of the new *Tiarella* were larger and had longer peduncles than plants of the cultivar Butterfly Wings.
2. Plants of the new *Tiarella* had larger leaves than plants of the cultivar Butterfly Wings.
3. Plants of the new *Tiarella* had simple leaves whereas plants of the cultivar Butterfly Wings had simple and compound leaves.
4. Plants of the new *Tiarella* and the cultivar Butterfly Wings differed in leaf markings.

Plants of the new *Tiarella* can be compared to plants of the male parent, the cultivar Lace Carpet. In side-by-side comparisons conducted by the Inventor in Scottdale, Pa., plants of the new *Tiarella* differed from plants of the cultivar Lace Carpet in the following characteristics:

1. Plants of the new *Tiarella* were larger and had longer peduncles than plants of the cultivar Lace Carpet.
2. Plants of the new *Tiarella* had larger leaves than plants of the cultivar Lace Carpet.
3. Plants of the new *Tiarella* and the cultivar Lace Carpet differed in leaf markings.
4. Lower surfaces of petals of the new *Tiarella* were white in color whereas lower surfaces of petals of the cultivar Lace Carpet were red purple in color.
5. Plants of the new *Tiarella* had thicker peduncles than plants of the cultivar Lace Carpet.

Plants of the new *Tiarella* can be compared to plants of the cultivar Elizabeth Oliver, not patented. In side-by-side comparisons conducted by the Inventor in Scottdale, Pa., plants of the new *Tiarella* differed from plants of the cultivar Elizabeth Oliver in the following characteristics:

1. Plants of the new *Tiarella* were larger and had longer peduncles than plants of the cultivar Elizabeth Oliver.
2. Plants of the new *Tiarella* had larger leaves with longer petioles than plants of the cultivar Elizabeth Oliver.
3. Plants of the new *Tiarella* and the cultivar Elizabeth Oliver differed in leaf markings.
4. Lower surfaces of petals of the new *Tiarella* were white in color whereas lower surfaces of petals of the cultivar Elizabeth Oliver were red purple in color.
5. Inflorescences of plants of the new *Tiarella* were not branched whereas inflorescences of plants of the cultivar Elizabeth Oliver were branched.

Plants of the new *Tiarella* can also be compared to plants of the cultivar Tiger Stripe, not patented. In side-by-side comparisons conducted by the Inventor in Scottdale, Pa., plants of the new *Tiarella* differed from plants of the cultivar Tiger Stripe in the following characteristics:

1. Leaves of plants of the new *Tiarella* were more deeply lobed than leaves of plants of the cultivar Tiger Stripe.
2. Lower surfaces of petals of the new *Tiarella* were white in color whereas lower surfaces of petals of the cultivar Tiger Stripe were red purple in color.
3. Plants of the new *Tiarella* had green-colored peduncles whereas plants of the cultivar Tiger Stripe had reddish green-colored peduncles.

BRIEF DESCRIPTION OF THE PHOTOGRAPHS

The accompanying colored photographs illustrate the overall appearance of the new *Tiarella*, showing the colors as true as it is reasonably possible to obtain in colored reproductions of this type. Colors in the photographs may differ slightly from the color values cited in the detailed botanical description which accurately describe the colors of the new *Tiarella*.

The photograph on the first sheet comprises a side perspective view of a typical flowering plant of 'Running Tiger'.

The photograph on the second sheet is a close-up view of a typical inflorescence of 'Shenandoah Mountain'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Scottdale, Pa. in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C. Measurements and numerical values represent averages taken from a group of flowering plants.

Botanical classification: *Tiarella cordifolia* cultivar Running Tiger.

Parentage:

*Female, or seed, parent.*—*Tiarella cordifolia* cultivar Butterfly Wings, disclosed in U.S. Plant Pat. No. 13,629.

*Male, or pollen, parent.*—*Tiarella cordifolia* cultivar Lace Carpet, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded plant habit with upright racemes with showy white-colored flowers. Vigorous and robust growth habit.

*Plant height, soil level to top of foliar plane.*—About 16 cm.

*Plant height, soil level to top of panicles.*—About 32 cm.

*Plant diameter or spread.*—About 25 cm.

*Foliage description.*—Arrangement: Basal rosette; simple. Length: About 10 cm. Width: About 7.5 cm. Shape: Cordate; palmately lobed. Apex: Acute. Base: Auriculate. Margin: Crenate with fine ciliation. Texture, upper and lower surfaces: Slightly rough; slightly pubescent. Venation pattern: Palmate; reticulate. Color: Developing leaves, upper surface: 144A to 143B, blotched with 59A. Developing leaves, lower surface: 144B. Fully expanded leaves, upper surface: 143B, blotched with 59A. Fully expanded leaves, lower surface: 144B. Venation, upper and lower surfaces: Same as lamina. Petiole: Length: About 12 cm. Diameter: About 1.5 mm. Texture, upper and lower surfaces: Pubescent. Color, upper and lower surfaces: Towards petiole base, 59C; towards leaf base, 144B.

Flower description:

*Appearance/arrangement.*—Single stellate flowers arranged on numerous erect, dense and cylindrical racemes; about 40 to 70 flowers and flower buds per flowering stem. Flowers face mostly outward to slightly upright. Flowers persistent. Flowers fragrant, sweet.

*Time of flowering.*—Under natural conditions, plants flower during May and June in Scottdale, Pa.; flowering continuous during this period.

*Inflorescence longevity.*—Individual inflorescences last about one week on the plant.

*Inflorescence size.*—Length: About 32 cm. Diameter: About 2.5 cm.

*Flower size.*—Diameter: About 8 mm. Depth (height): About 6 mm.

*Flower buds.*—Height: About 3 mm. Diameter: About 2.5 mm. Shape: Bulbous. Color, at stage of showing color: 62D.

*Calyx.*—Quantity/arrangement: Five sepals; radially symmetrical; base fused. Length: About 3.5 mm. Diameter: About 6 mm. Shape: Cupped; sepals, ovate. Sepal apex: Obtuse. Sepal margin: Entire. Texture, upper and lower surfaces: Pubescent. Color: When opening and fully opened, upper surface: Close to 155D. When opening and fully opened, lower surface: Close to 155D.

*Petals.*—Quantity/arrangement: Five sepals; radially symmetrical. Length: About 4 mm. Width: About 1 mm. Shape: Spatulate. Apex: Acute. Margin: Entire. Texture, upper and lower surfaces: Pubescent. Color:

When opening and fully opened, upper surface: Close to 155D. When opening and fully opened, lower surface: Close to 155D shaded with 62D.

*Flower bracts.*—Length: About 2 mm. Width: About 0.8 mm. Shape: Lanceolate. Apex: Acute. Margin: Ciliate. Texture, upper and lower surfaces: Smooth. Color, upper and lower surfaces: 144A.

*Peduncle.*—Strength: Strong; flexible. Aspect: Mostly upright. Length: About 25 cm. Diameter: About 1.8 mm. Texture: Smooth. Color: 144A.

*Pedicels.*—Strength: Strong; wiry. Aspect: About 10 to 30° from vertical. Length: About 6 mm. Diameter: About 0.5 mm. Texture: Pubescent. Color: 144A.

*Reproductive organs.*—Androecium: Stamen number: Ten per flower. Anther shape: Oval. Anther length: About 0.2 mm. Anther color: 25B. Amount of pollen: Moderate. Pollen color: 16B. Gynoecium: Pistil number: One per flower. Pistil length: About 5 mm. Stigma shape: Rounded. Stigma color: 157C. Style length: About 3 mm. Style color: 157C. Ovary color: 157C.

*Seed/fruit.*—Seed and fruit production have not been observed.

Disease/pest resistance: Resistance to pathogens and pests common to *Tiarella* has not been observed on plants grown under commercial conditions.

Temperature tolerance: Plants of the new *Tiarella* have demonstrated good tolerance to night temperatures as low as −35° C. and day temperatures as high as 40° C.

It is claimed:

1. A new and distinct cultivar of *Tiarella* plant named 'Running Tiger', as illustrated and described.

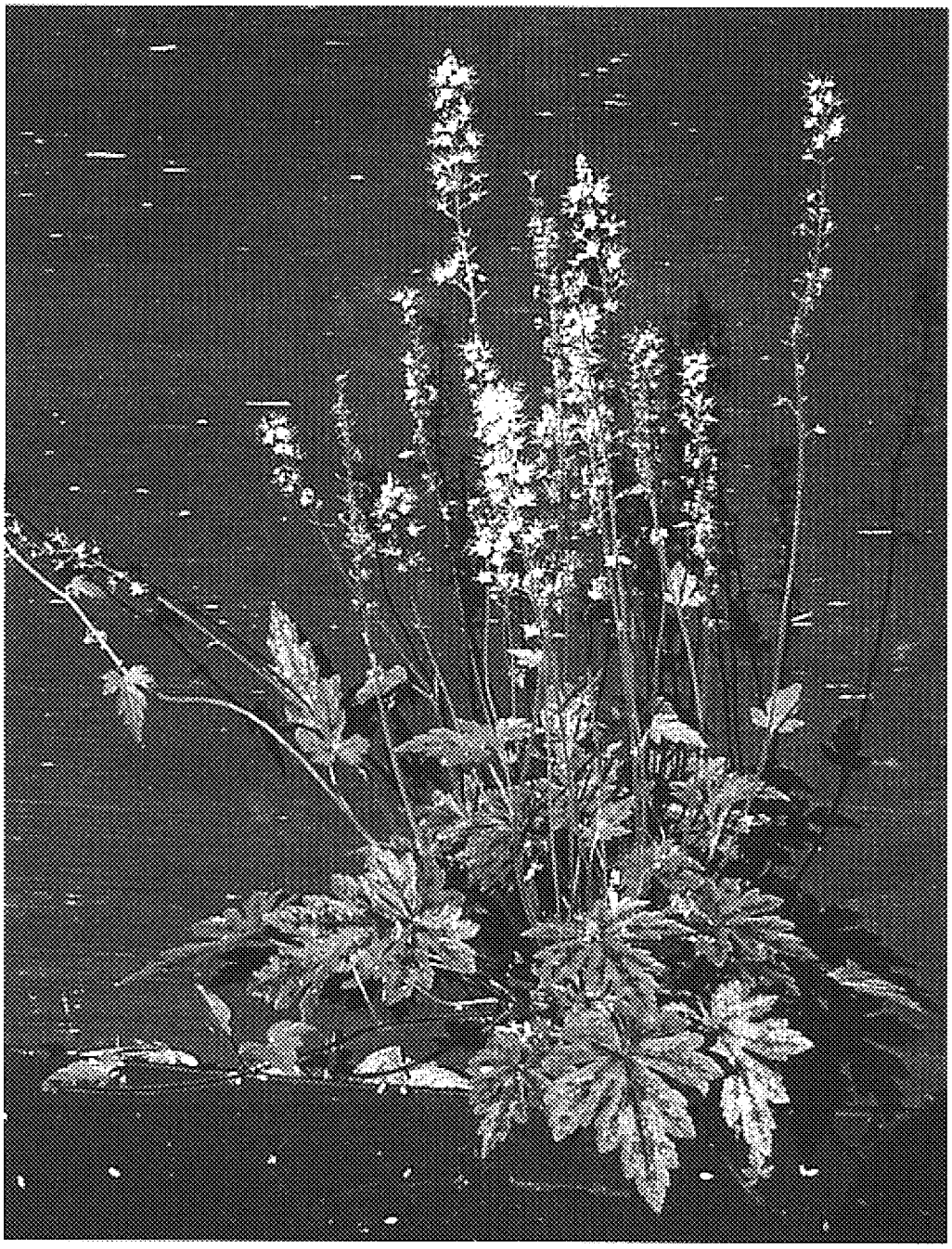

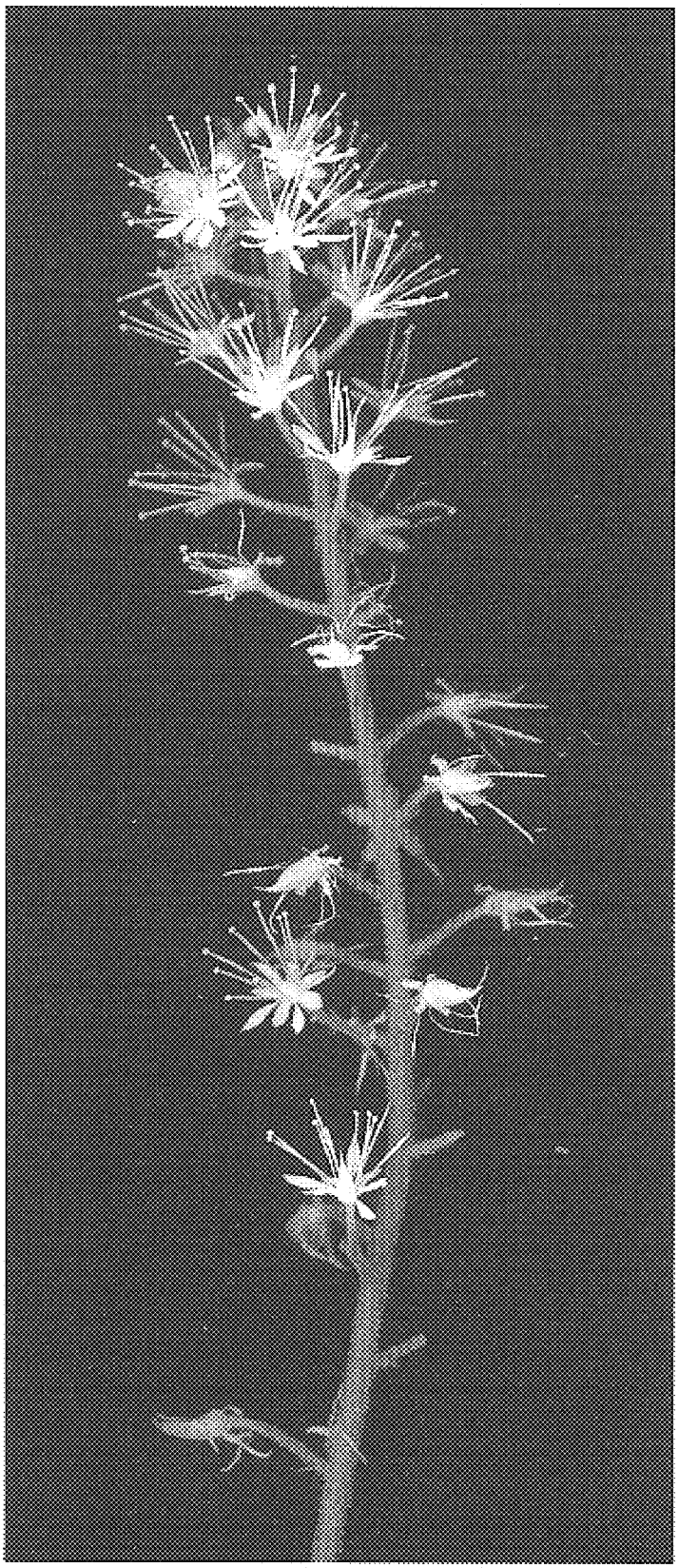

* * * * *